United States Patent
Kwon et al.

(10) Patent No.: US 7,435,216 B2
(45) Date of Patent: Oct. 14, 2008

(54) ROBOTIZED LAPAROSCOPIC SYSTEM

(75) Inventors: Dong Soo Kwon, Daejeon (KR); Seong Young Ko, Seoul (KR); Jonathan Kim, Flushing, NY (US); Yun Ju Lee, Busan (KR); Woo Jung Lee, Seoul (KR)

(73) Assignee: Korea Advanced Institute of Science and Technology (KR)

( * ) Notice: Subject to any disclaimer, the term of this patent is extended or adjusted under 35 U.S.C. 154(b) by 263 days.

(21) Appl. No.: 10/971,249

(22) Filed: Oct. 22, 2004

(65) Prior Publication Data
US 2005/0240078 A1 Oct. 27, 2005

(30) Foreign Application Priority Data
Apr. 22, 2004 (KR) .................... 10-2004-0027949

(51) Int. Cl.
*A61B 1/00* (2006.01)
(52) U.S. Cl. .................... 600/139; 600/101; 600/117; 600/145; 600/146
(58) Field of Classification Search ............. 600/112, 600/114, 101, 106, 117, 118, 137, 139, 145, 600/146; 606/130; 128/898
See application file for complete search history.

(56) References Cited

U.S. PATENT DOCUMENTS

| | | | |
|---|---|---|---|
| 4,108,211 A | | 8/1978 | Tanaka |
| 4,273,111 A | | 6/1981 | Tsukaya |
| 4,503,842 A | | 3/1985 | Takayama |
| 5,159,446 A | * | 10/1992 | Hibino et al. .................. 348/65 |
| 5,400,769 A | * | 3/1995 | Tanii et al. .................. 600/152 |
| 5,815,640 A | | 9/1998 | Wang et al. |
| 6,097,423 A | * | 8/2000 | Mattsson-Boze et al. ...... 348/65 |
| 6,162,171 A | * | 12/2000 | Ng et al. ..................... 600/141 |
| 6,551,237 B2 | | 4/2003 | Matsui |
| 6,569,086 B2 | | 5/2003 | Ono et al. |
| 6,669,629 B2 | | 12/2003 | Matsui |
| 6,699,179 B2 | * | 3/2004 | Wendlandt .................. 600/114 |
| 6,872,178 B2 | * | 3/2005 | Weinberg .................... 600/114 |
| 2003/0050649 A1 | * | 3/2003 | Brock et al. ................. 606/130 |

(Continued)

OTHER PUBLICATIONS

Yun-Ju Lee et al., "Design of a Compact Laparoscopic Assistant Robot: KaLAR," ICCAS2003, Oct. 22-25, 2003(5 pages).

*Primary Examiner*—John P. Leubecker
*Assistant Examiner*—Victoria W Chen
(74) *Attorney, Agent, or Firm*—Brinks Hofer Gilson & Lione (57) ABSTRACT

A robotized laparoscopic system capable of executing commands of an operating surgeon is provided. The laparoscopic system includes a cylindrical tube inserted through an incision. A small-sized camera is attached to one end of the tube to capture the images of the surgical site. A bending portion is adapted to bend the tip of the tube in any direction. A driving unit controls a bending direction and a bending angle of the bending portion. A movement device moves the tube forward or backward in a longitudinal direction. A control unit independently controls the driving unit and the movement device. An input unit receives commands from the surgeon. A conversion unit converts the command input from the surgeon into digital signals and transmits the digital signals to the control unit. A support unit supports the weight of the movement device by being connected to an operating table or the floor.

1 Claim, 7 Drawing Sheets

U.S. PATENT DOCUMENTS

| | | | |
|---|---|---|---|
| 2003/0055410 A1* | 3/2003 | Evans et al. | 606/1 |
| 2003/0189768 A1* | 10/2003 | Murayama | 359/782 |
| 2004/0138527 A1* | 7/2004 | Bonner et al. | 600/114 |
| 2004/0225185 A1* | 11/2004 | Obata et al. | 600/118 |
| 2004/0243147 A1* | 12/2004 | Lipow | 606/130 |

* cited by examiner

EXAMINATION REGION

ROBOTIZED LAPAROSCOPIC SYSTEM

PRIORITY CLAIM

This application claims under 35 U.S.C. § 119 the benefit of the filing date of Apr. 22, 2004 of Korean Application No. 2004-27949, the entire contents of which are incorporated herein by reference.

BACKGROUND

1. Technical Field

The invention generally relates to a laparoscopic system and, more particularly, to a robotized laparoscopic system capable of executing a surgeon's commands.

2. Related Art

A laparoscopic system visualizes a surgical site through a tube inserted through an opening in the abdominal walls. Various surgical instruments such as surgical scalpels, surgical needles, etc. are generally used with a laparoscope. A surgeon in charge of surgery normally operates surgical instruments, whereas an assistant helping a surgeon operates a laparoscope during the surgery. An assistant operates the laparoscope according to commands from a surgeon and communications between a surgeon and an assistant are very important to achieve a successful laparoscopic surgery. However, many factors such as difference in the level of expertise frequently undermine accurate and effective communications, i.e., issuing and following commands, between a surgeon and an assistant, and the inaccurate communications may adversely affect outcome of a surgery.

Figure 1:
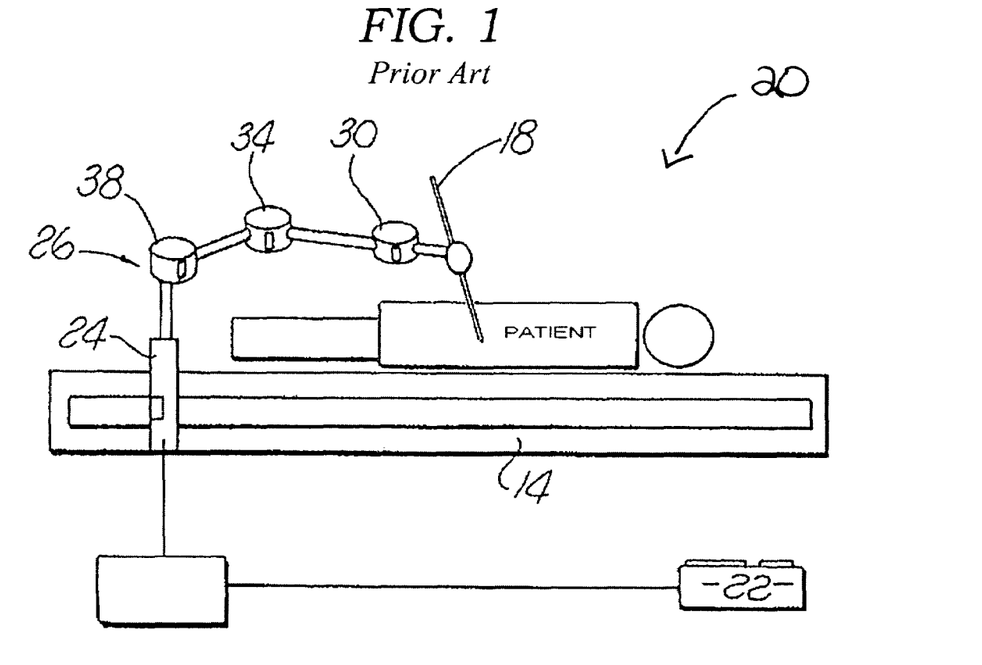
FIG. 1 shows a conventional automated endoscope system.

U.S. Pat. No. 5,815,640 discloses an automated endoscope system for optimal positioning as illustrated in FIG. 1. This system 20 is constructed to mount a robotic arm 26 that replaces an assistant who maneuvers a conventional rigid endoscope 18. The robotic arm 26 includes a plurality of actuators 24, 30, 34 and 38 and is operated by a foot pedal 22 above an operating table 14. Accordingly, a surgeon can control a movement of the endoscope 18 by directly manipulating the foot pedal 22. However, the system creates distractions to a surgeon because of a large motion of the robotic arm 26 actuated by multiple joints. Further, a plurality of actuators 24, 30, 34 and 38 are needed to generate a required motion, which increases manufacturing costs and size of the system.

In addition, the endoscope 18 is inserted into an abdominal cavity through a trocar, which is a sharp-pointed surgical instrument fitted with a cannula. The robotic arm 26 pivotally moves, which is created by the insertion of a trocar, to change viewing angle to the abdominal cavity. However, in case of thyroidectomy or sternotomy, formation of a pivot is impossible and this system 20 may not apply to these surgeries. Further, an additional device needs to be installed.

Figure 2:
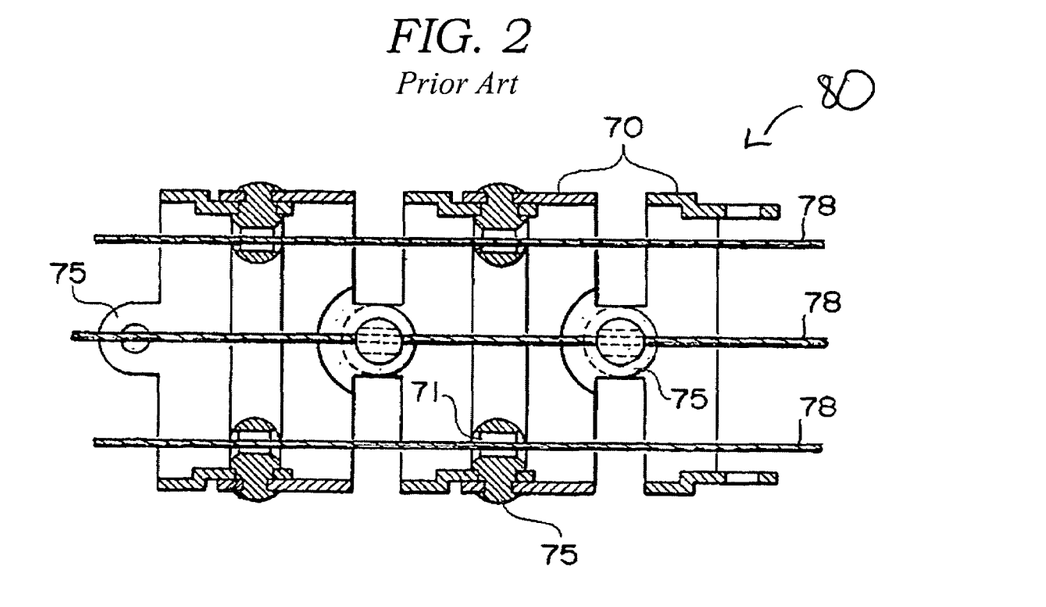
FIG. 2 shows a conventional articulated tube structure.

U.S. Pat. No. 4,108,211 discloses four-way bendable tube structure, as shown in FIG. 2. The tube structure 80 is articulate and includes a plurality of links 70 connected by joints 75 and wire guides 71. Two pairs of wires 78 passing through the tube structure 80. The joints 75 formed at both ends are alternatively connected to allow continuously connected links 70 to turn in opposite directions. The wires 78 run from actuators to the most distal link among the links 70. If the actuators are activated, pulling the wires 78 causes a change in tension of the wires and results in bending of the links 70. Therefore, if the wires 78 wound by the actuators are controlled, the direction in which the links 70 are bent is easily adjustable. Accordingly, such an articulated structure can be effective when it is used with a laparoscope, in particular where dexterous movement is required in a narrow place.

In addition, U.S. Pat. Nos. 4,273,111, 4,503,842, 6,551,237, 6,569,086 and 6,669,629 discloses conventional systems that are applicable to an endoscope. However, the systems disclosed in the above-mentioned patents cannot apply to a laparoscopy. Because they are designed to inspect human organs through tortuous intestines, an accurate and detailed control of motions is not possible. Furthermore, a surgeon needs to use a specific input device or the help of an assistant to operate the systems. Accordingly, there is a need of a system that overcomes the foregoing drawbacks of the conventional system.

SUMMARY

One aspect of the invention is a robotized laparoscopic system capable of executing the operating surgeon's commands and steadily displaying a surgical site by automatically maneuvering or in response to a surgeon's commands. The laparoscopic system includes a cylindrical penetration tube, a camera, a driving unit and a control unit. The cylindrical penetration tube can be inserted into an opening through a trocar. The camera is attached at a tip of the penetration tube for displaying images of the surgical site. A bending portion is disposed adjacent to the tip for bending the penetration tube in any direction. The driving unit controls bending direction and angle of the bending portion. The laparoscopic system further includes a movement device, a control unit, a conversion unit and an input unit. The movement device moves the penetration tube forward or backward in a longitudinal direction. The control unit independently controls the driving unit and the movement device. The input unit receives commands from a surgeon, and the conversion unit converts command input from a surgeon into digital signals and transmitting them to the control unit.

Other systems, methods, features and advantages of the invention will be, or will become, apparent to one with skill in the art upon examination of the following figures and detailed description. It is intended that all such additional systems, methods, features and advantages be included within this description, be within the scope of the invention, and be protected by the following claims.

BRIEF DESCRIPTION OF THE DRAWINGS

The invention can be better understood with reference to the following drawings and description. The components in the figures are not necessarily to scale, emphasis instead being placed upon illustrating the principles of the invention. Moreover, in the figures, like referenced numerals designate corresponding parts throughout the different views.

DETAILED DESCRIPTION OF THE PREFERRED EMBODIMENTS

Figure 3:
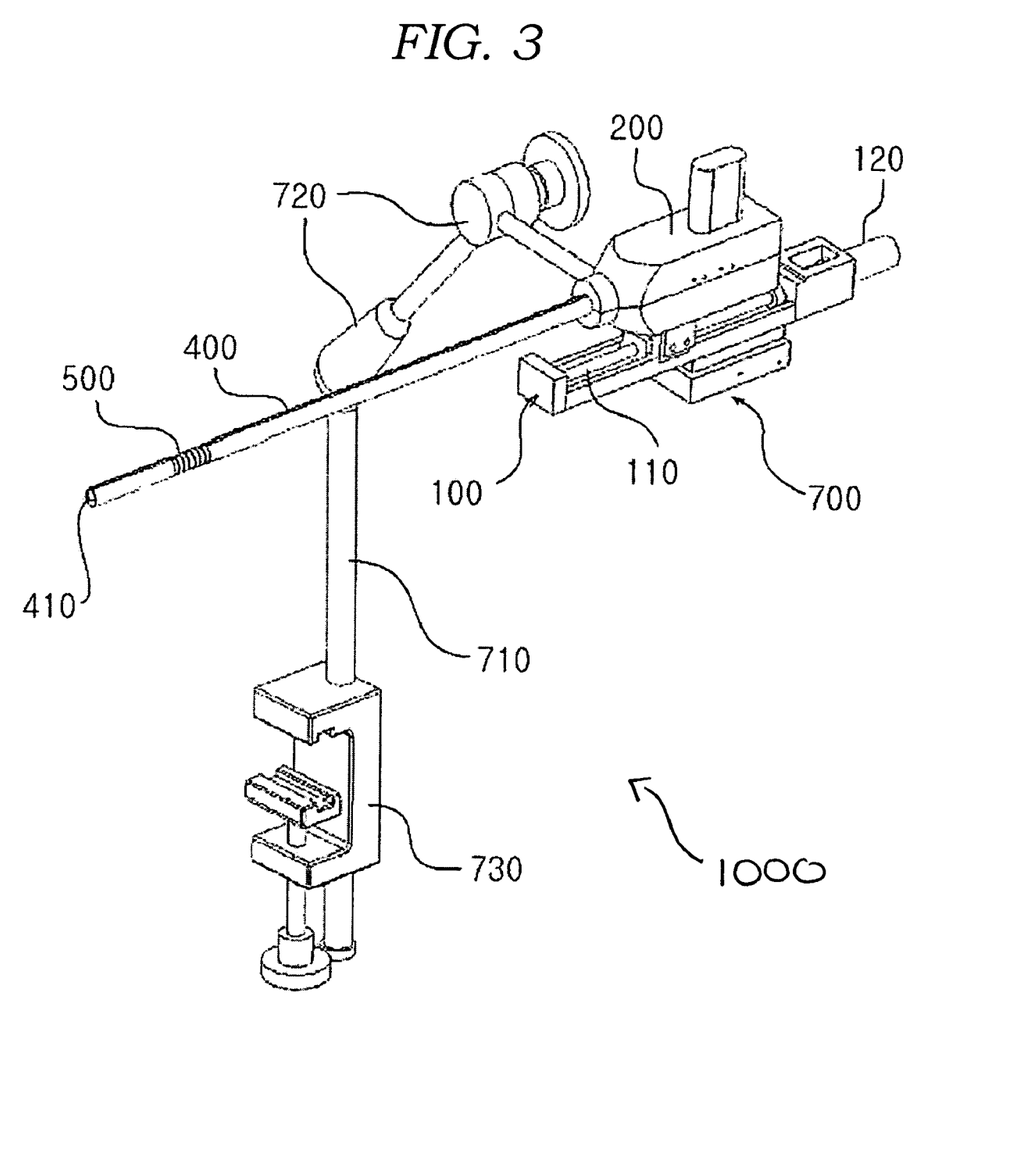
FIG. 3 is a perspective view showing one embodiment of a robotized laparoscopic system.

FIG. 3 shows one embodiment of a robotized laparoscopic system, which is capable of executing a surgeon's commands. A laparoscopic system 1000 includes a guide unit 100, a bending actuator housing 200 and a penetration tube 400. The guide unit 100 supports the bending actuator housing 200 and other portions and is coupled to a support unit 700. The support unit 700 is fixed on an operating table or floor. The support unit 700 includes a fixture 730 that is able to be easily fastened and clamped to the operating table and a support rod 710 that supports the guide unit 100 to maintain its height from the operating table at a certain level. A plurality of joints 720 are coupled to the support rod 710 and spaced apart from each other at a predetermined distance to adjust the position and orientation of the guide unit 100.

Figure 4:
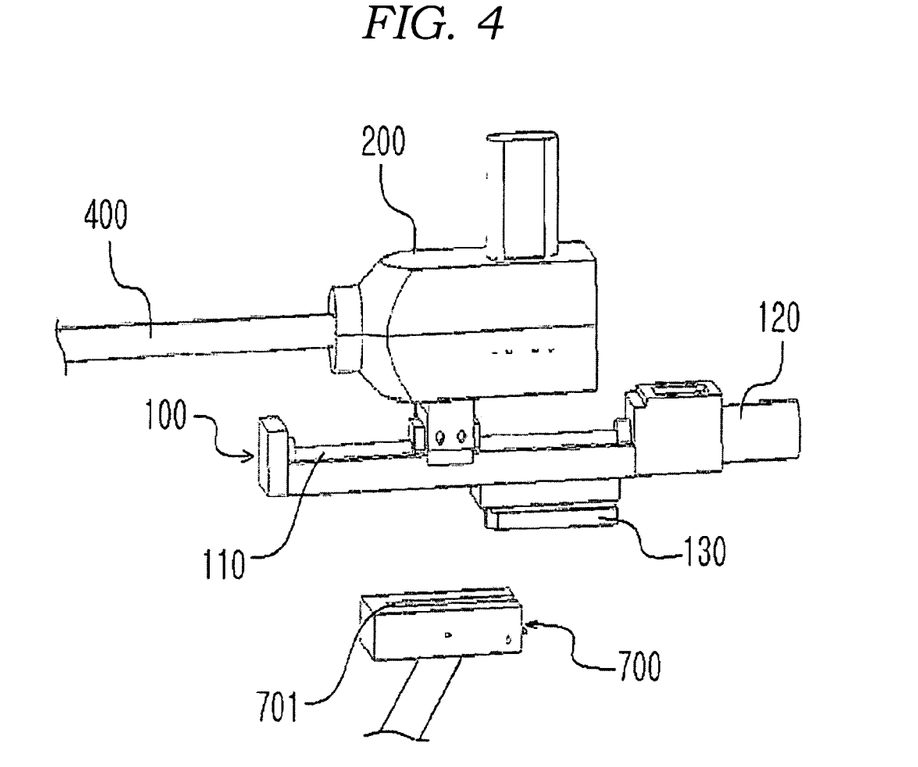
FIG. 4 shows an embodiment of support detached from an embodiment of a bending actuator housing in the laparoscopic system of FIG. 3.

FIG. 4 illustrates in detail the guide unit 100 coupled to the support unit 700. A protrusion 130 is inserted into a groove 701 of the support unit 700, which enables the guide unit 100 and the support unit 700 to be easily attached to or detached from each other. A guide rail 110 and a linear motor 120 are mounted on the guide unit 100 to linearly reciprocate the bending actuator housing 200. The housing 200 is mounted on the guide rail 110, and linearly reciprocates by the linear motor 120 along the guide rail 110. Thus, the guide unit 100, the housing 200 and the motor 120 define a movement device for the tube 400.

One end of the bending actuator housing 200 is coupled to the penetration tube 400. Referring again to FIG. 3, a small-sized camera 410 is installed for visualizing the images of a surgical site at one end of the penetration tube 400. A bending portion 500 adjacent to the tip of the penetration tube 400 is provided. In this embodiment, the camera 410 is coupled to the tip of the penetration tube 400. The camera 410 is proximately placed to a surgical site, so that an intermediate image transfer device is not needed and resolution of images of the surgical site increases. Alternatively or additionally, the camera 410 may be installed in the center of the penetration tube 400 or in the bending actuator housing 200. In that case, structures for transmitting images such as a bundle of optical fibers are connected from the tip of the penetration tube 400 to the camera 410 to transmit images acquired at the tip of the penetration tube 400 to the camera 410.

Figure 5:
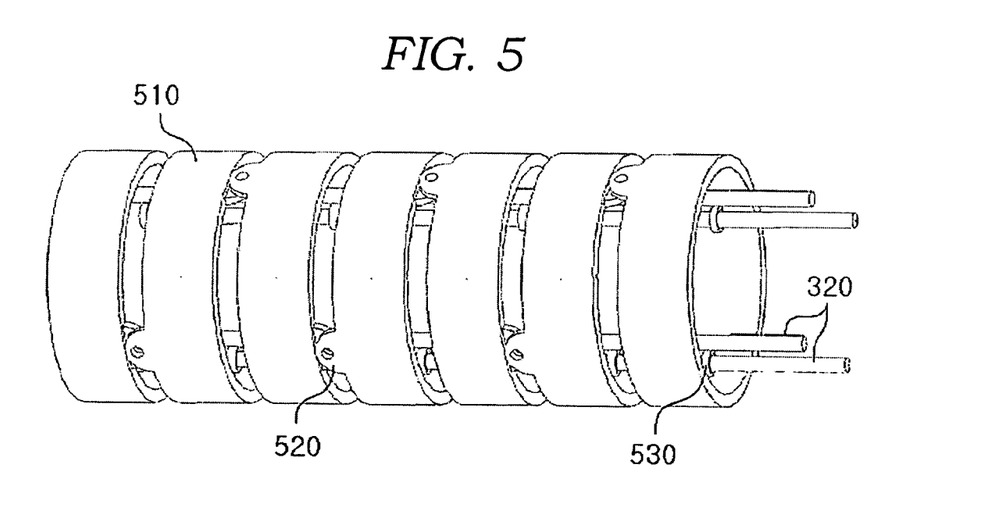
FIG. 5 shows an embodiment of a bending portion of the laparoscopic system of FIG. 3.
Figure 6:
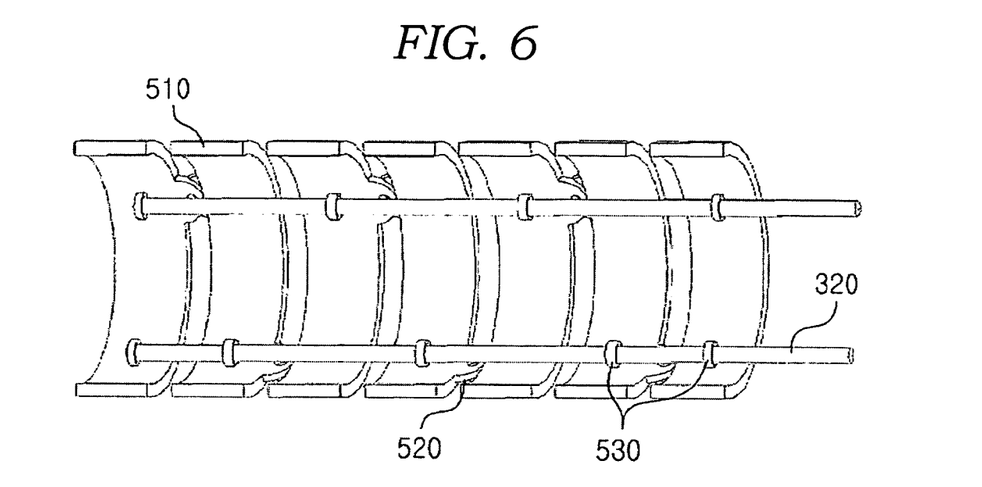
FIG. 6 is a sectional view of the bending portion of FIG. 5.

FIGS. 5-6 show an enlarged view of the bending portion 500 shown in FIG. 3. The bending portion 500 includes a plurality of annular link members 510. Each link member 510 has a pair of joints 520 at its both ends. Two joints 520 cross from each other at an angle of 90 degrees, so that they have rotating radii perpendicular to each other. Due to the link members 510, bending direction of the bending portion 500 is not limited to any specific direction.

FIG. 6 shows a sectional view of the bending portion 500. A plurality of wire guides 530 is formed on the inner surface of the link members 510 in four directions of the link members 510, and wires 320 are inserted into the wire guides 530. The wire guides 530 on the inner surfaces of the link members 510 are formed to be co-linear when the bending portion 500 is straightened. The wire guides 530 of the last link member 510 are coupled to the wires 320. Therefore, if one of the four wires 320 coupled to the last joint member 510 is released at a certain length, the other wire opposite to the released wire 320 is drawn at the same length. Accordingly, intervals between the joint members 510 on one side decrease and intervals between the joint members 510 on the other side increase due to the wires 320, thereby bending the bending portion 500.

Figure 7:
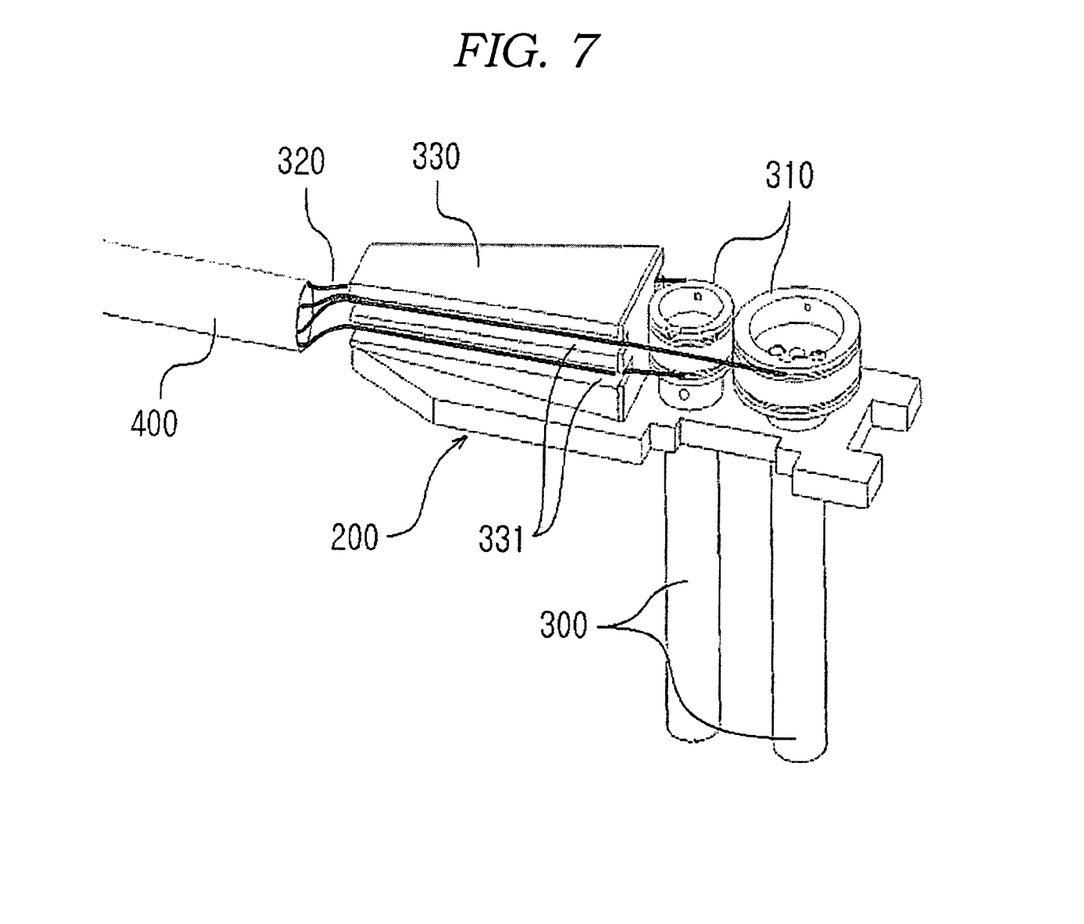
FIG. 7 is an embodiment of a driving unit of the laparoscopic system of FIG. 3.

FIG. 7 shows a driving unit of the laparoscopic system 1 shown in FIG. 3. As shown in FIG. 7, two motors 300 and two circular bobbins 310 are installed within the bending actuator housing 200. The rotational axes of the circular bobbins 310 are connected to the motors 300, respectively. Four wires 320 connecting link members 510 are wound around the two bobbins 310, so that two wires 320 are wound around upper and lower portions of one bobbin. When each of the wires 320 is extended to the penetration tube 400 having a small diameter, the wires 320 may become tangled. For this reason, a guide member 330 having a plurality of guide grooves 331 is installed. The wires 320 wound around the circular bobbins 310 are extended to an inlet of the penetration tube 400 without getting tangled. On the guide member 330, the guide grooves 331 are formed to allow the wires 320 to be separately inserted therein.

Figure 8:
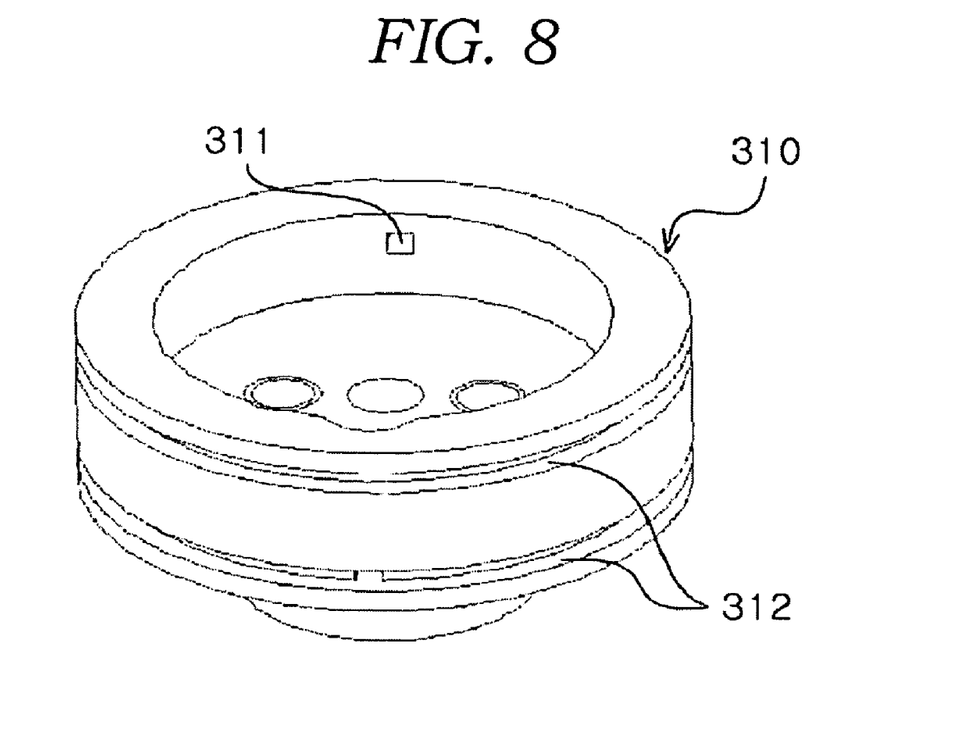
FIG. 8 is an enlarged view showing an embodiment of a circular bobbin used with the driving unit of FIG. 7.

FIG. 8 is an enlarged view of a circular bobbin 310. Holes 311 are formed on the circular bobbin 310 to allow the wires 320 to be fastened thereto. Grooves 312 formed on the bobbin 310 restrict the movement of the wires 320. A pair of wires 320 wound around the circular bobbin 310 are wires 320 that are to be inserted into opposite wire guides 530 of the bending portion 500 and are wound around the circular bobbin 310 in opposite directions. Therefore, if the circular bobbin 310 is rotated in any one direction, one wire 320 is wound and the other wire 320, forming a pair with the wire 320, is released. At this time, the last link member 510 of the bending portion 500 is coupled to the wires 320, so that a side of the bending portion 500 is contracted or extended with the rotation of the circular bobbin 310. If the operating directions of the two motors 300 are suitably adjusted, the bending direction of the bending portion 500 can be arbitrarily controlled. However, at the joints 520 of the bending portion 500, slight spaces exist to facilitate the driving of the bending portion 500, and revolutions of the motors 300 is not always proportional to the bending angle of the bending portion 500 due to the spaces. Therefore, an elastic member is coupled to the inner or outer side of the bending portion 500 in the longitudinal direction of the bending portion 500. This enables the rotary angle of the motors 300 and the bending angle of the bending portion 500 to be proportional to each other.

Figure 9:
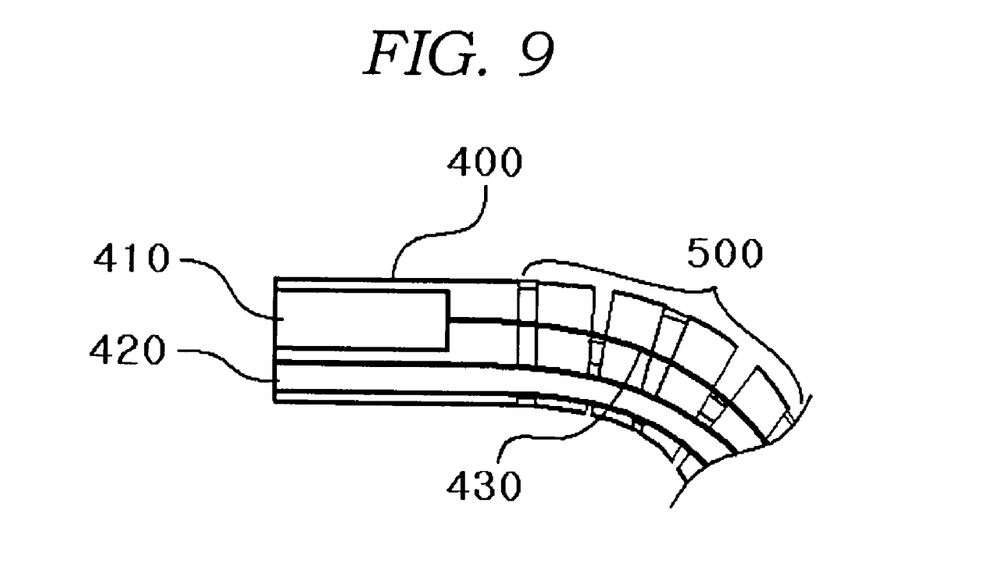
FIG. 9 is a sectional view showing an embodiment of a penetration tube of the laparoscopic system of FIG. 3.
Figure 10:
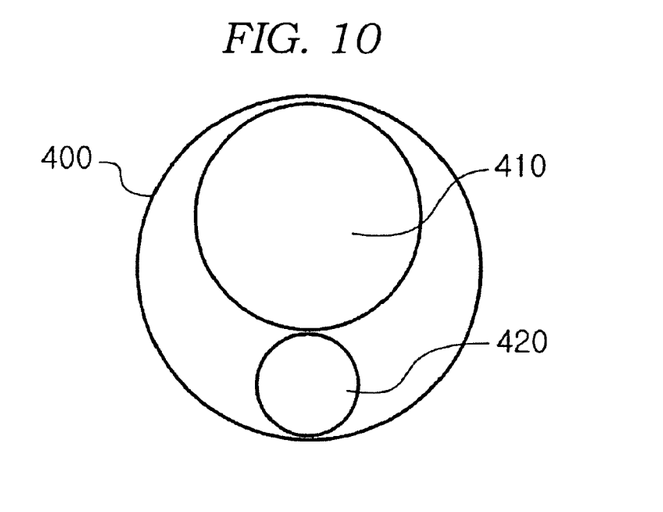
FIG. 10 is a front view showing the penetration tube of FIG. 9.

FIGS. 9-10 show a bending portion of the penetration tube 400 in detail. At the tip of the penetration tube 400, the small-sized camera 410 and a light transmission unit 420 are installed. The small-sized camera 410 is connected to an external output device or power device through an electric wire 430, and the light transmission unit 420 is connected to an external light source device. The bending portion 500 is placed on the end tip of the penetration tube 400, so that the angle of the small-sized camera 410 is be adjusted by operating the motors 300.

FIG. 10 shows a front view of the penetration tube 400 shown in FIG. 9. The end tip of the light transmission unit 420 is installed below the small-sized camera 410, but the position of the light transmission unit 420 is not limited to this embodiment. Depending on the size of the light transmission unit 420 and the small-sized camera 410, the position and the number of light transmission units 420 to be installed can be adjusted. While a surgeon performs surgery using surgical images captured by the small-sized camera 410, he or she needs to rotate the captured images relative to the longitudinal axis of the penetration tube 400. An auxiliary driving device (not shown) may be installed on the penetration tube 400. The auxiliary driving device is capable of rotating the small-sized camera 410 relative to the longitudinal axis of the penetration tube 400.

Figure 11:
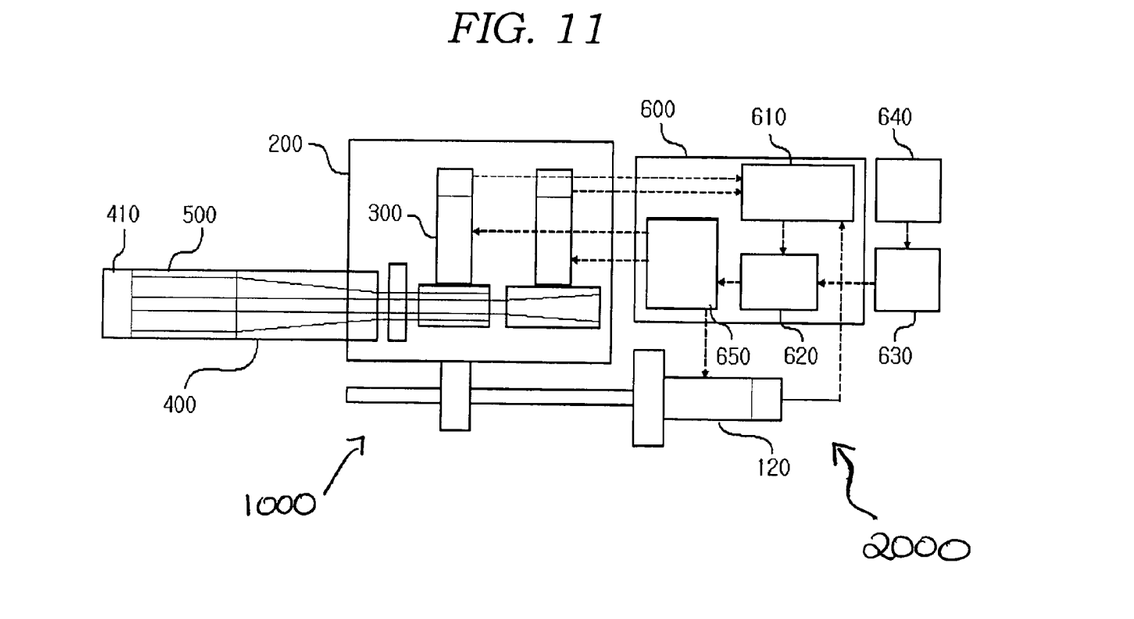
FIG. 11 shows the brief construction of the laparoscopic system of FIG. 3.

FIG. 11 is a block diagram of an entire system 2000 including the laparoscopic system 1000 of FIG. 3. The system 2000 includes a control unit 600, an input unit 640 and a conversion unit 630. As described above, the wires 320 coupled to the bending portion 500 are wound around the circular bobbins 310. The bending actuator housing 200 coupled to the penetration tube 400 can move along the guide rail 110 of the guide unit 100. Therefore, the view of a surgical site is determined by the operation of the motors 300 that rotate the circular bobbins 310, and the enlargement/reduction ratio of the view is determined by the operation of the linear motor 120 that moves the penetration tube 400 forward or backward.

A conventional rigid laparoscope is manipulated by an assistant on behalf of the operating surgeon and provides a surgeon with a different view from that of an assistant. To the contrary, the system 2000 including the laparoscopic system 1000 is directly operated by a surgeon performing an operation. A surgeon input commands to the input unit 640 and the control unit 600 operates the motors 300 and the linear motor 120 based on a command input. A conversion unit 630 is interposed between the input unit 640 and the control unit 600 and converts a surgeon's commands into corresponding movement commands of each motor. Then, the conversion unit 630 transmits these control signals to the control unit 600.

The control unit 600 further includes a counter 610 and a computation unit 620. The counter 610 measures revolutions of the motors 300 and the movement distance of the linear motor 120. The computation unit 620 calculates the motor input corresponding to the position difference between the surgeon's command input position and the current tip position of the penetration tube 400. The control unit 630 also includes a motor driving unit 650 for operating the motors 300 and the linear motor 120. These units help a surgeon to more precisely adjust the position of the small-sized camera 410 while performing an operation. In this embodiment, a microphone device for receiving commands from the surgeon is used as the input unit 640. Alternatively or additionally, the input unit 640 may include a position measurement device for measuring the location of a surgeon's head, a foot pedal switch or a joystick.

Figure 12:
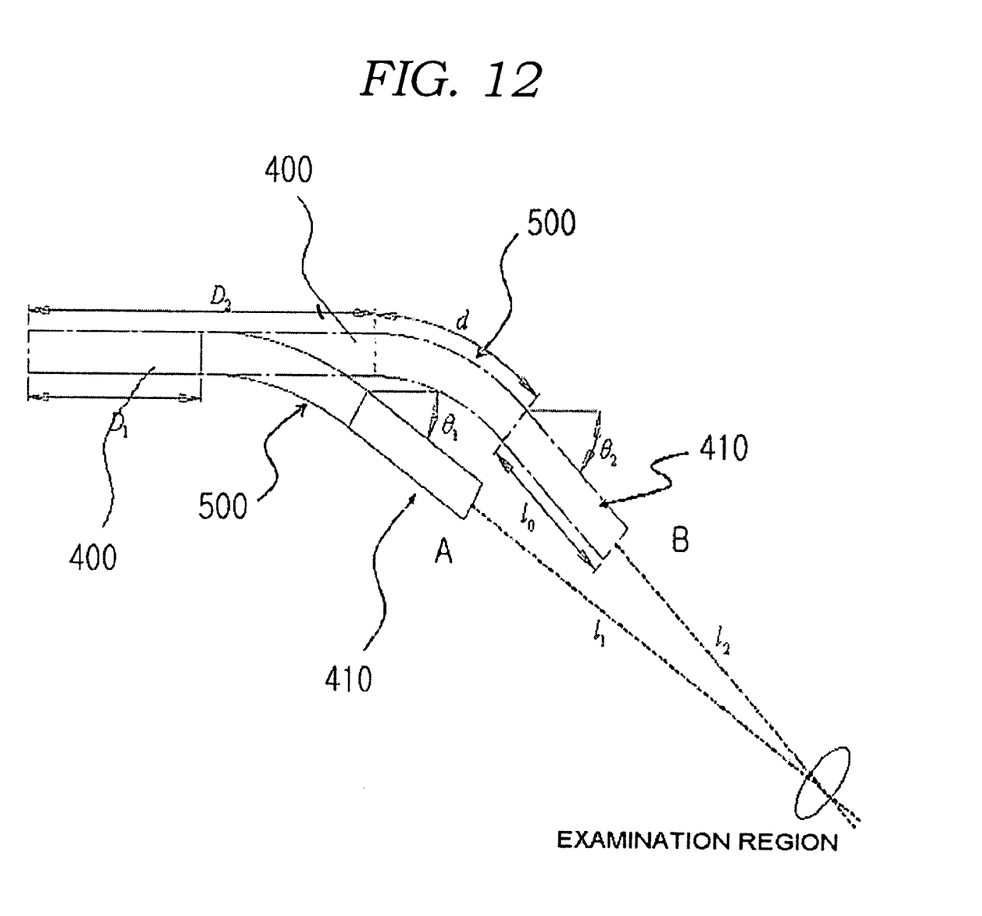
FIG. 12 shows an operating status to implement enlarged and reduced images using the laparoscopic system of FIG. 3.

FIG. 12 shows an operating status of the laparoscopic system 1000. Generally, the camera 410 installed at the penetration tube normally has no enlargement and reduction functions due to its small size. Instead of the camera 410, the laparoscopic system 1000 generates the enlargement and reduction functions of the camera by moving the penetration tube 400 forward or backward. However, if the penetration tube 400 is moved forward or backward while being bent, the viewing angle by the small-sized camera 410 changes and therefore, a separate control method is required. As shown in FIG. 12, if the penetration tube 400 moves forward from position A and the direction of the small-sized camera 410 is not adjusted, the view captured by the small-sized camera 410 may change. Therefore, in order to correct the difference in position of an image due to the forward movement of the penetration tube 400, the bending portion 500 should be bent at the same time as the penetration tube 400 moves forward, for example, to the position B.

The following Equations [1] and [2] can be derived on the basis of the relationship between positions A and B.

$$\frac{d}{\theta_1}(1-\cos\theta_1) + (l_0+l_1)\sin\theta_1 = \frac{d}{\theta_2}(1-\cos\theta_2) + (l_0+l_2)\sin\theta_2 \quad [1]$$

$$\frac{d}{\theta_1}\sin\theta_1 + (l_0+l_1)\cos\theta_1 + D_1 = \frac{d}{\theta_2}\sin\theta_2 + (l_0+l_2)\cos\theta_2 + D_2 \quad [2]$$

where $D_1$ is position of the penetration tube 400 relative to the guide unit 100 at position A and $D_2$ is the position of the penetration tube 400 relative to the guide unit 100 at position B;

d is the length of the bending portion 500;

$I_0$ is the length between the lens of the small-sized camera 410 and the bending portion 500; $I_1$ is the distance between the lens of the small-sized camera 410; and the surgical site of interest and $I_2$ is the distance between the lens of the small-sized camera 410 and the surgical site of interest.

In order to perform enlargement and reduction, the position of the linear motor 120 and the bending angle of the bending portion 500 must be calculated. Specifically, to perform either enlargement or reduction, when the desired distance varies from $I_1$ to $I_2$, variations occurring in the movement from $D_1$ to $D_2$ and variations occurring in the movement from $\theta_1$ to $\theta_2$ must be obtained. The $\theta_2$ can be obtained by solving Equation [1], and $D_2$ can be obtained using the $\theta_2$ and Equation [2].

Equations [1] and [2] are calculated by the control unit 600 and/or the conversion unit 630. If an enlargement or reduction command has been issued by the surgeon, the control unit 600 and the conversion unit 630 automatically calculate $\theta_2$ and $D_2$ to calculate the amount of the movement of the motors 300 and the linear motor 120, thus operating both the motors 300 and the linear motor 120 based on the calculation of the amount of the movement.

A robotized laparoscopic system is capable of executing the operating surgeon's commands during surgery even where the formation of a pivot is impossible. The laparoscopic system can reduce distractions between a surgeon and the robotized laparoscopic system by minimizing movements of the system outside the abdominal cavity while providing internal images of equivalent quality as a conventional system. The laparoscopic system is compact and light-weight, which allows a surgeon to perform laparoscopy without the help of an assistant. Further, operation costs can be reduced. In addition, a surgeon can perform an operation more precisely by directly maneuvering the camera using 3 degrees-of-freedom motion.

While various embodiments of the invention have been described, it will be apparent to those of ordinary skill in the art that many more embodiments and implementations are possible within the scope of the invention. Accordingly, the invention is not to be restricted except in light of the attached claims and their equivalents.

We claim:

1. A robotized laparoscopic system for a surgery, comprising:
   a cylindrical tube adapted to be inserted through an incision on abdominal walls and having a tip on one end;
   a bending portion for connecting the cylindrical tube and the tip and for changing a bending direction of the tip;
   a driving unit for controlling the bending direction and a bending angle of the bending portion;
   a movement device for moving the tube in a longitudinal direction; and
   a control unit for controlling the driving unit and the movement device independently;

wherein the control unit calculates a rotation angle $\theta_2-\theta_1$ of the bending portion during a longitudinal displacement $D_2-D_1$ of the movement device using the following Equations, to compensate for the change in viewing angle by either enlargement or reduction command:

$$\frac{d}{\theta_1}(1-\cos\theta_1) + (l_0+l_1)\sin\theta_1 = \frac{d}{\theta_2}(1-\cos\theta_2) + (l_0+l_2)\sin\theta_2$$

$$\frac{d}{\theta_1}\sin\theta_1 + (l_0+l_1)\cos\theta_1 + D_1 = \frac{d}{\theta_2}\sin\theta_2 + (l_0+l_2)\cos\theta_2 + D_2$$

where d is a length of the bending portion, $I_0$ is a distance between a front surface of the tube and the bending portion, $\theta_1$ is a bending angle of the bending portion before moving, $I_1$ is a distance between an end of the tube and a surgical site of interest before moving, $D_1$ is a position of the tube before moving, $\theta_2$ is a bending angle of the bending portion after moving, $I_2$ is a distance between the tip of the tube and the surgical site after moving, and $D_2$ is a position of the tube after moving.

* * * * *